(12) United States Patent
Wang et al.

(10) Patent No.: US 8,946,484 B2
(45) Date of Patent: Feb. 3, 2015

(54) METHOD FOR PRODUCING PHENOL AND/OR CYCLOHEXANONE

(75) Inventors: Kun Wang, Bridgewater, NJ (US); Roberto Garcia, Easton, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 14/009,827

(22) PCT Filed: Dec. 15, 2011

(86) PCT No.: PCT/US2011/065063
§ 371 (c)(1),
(2), (4) Date: Dec. 18, 2013

(87) PCT Pub. No.: WO2012/145032
PCT Pub. Date: Oct. 26, 2012

(65) Prior Publication Data
US 2014/0296577 A1    Oct. 2, 2014

Related U.S. Application Data

(60) Provisional application No. 61/476,893, filed on Apr. 19, 2011.

(51) Int. Cl.
| | |
|---|---|
| *C07C 45/53* | (2006.01) |
| *C07C 37/08* | (2006.01) |
| *C07C 15/067* | (2006.01) |
| *C07C 407/00* | (2006.01) |
| *C07C 2/66* | (2006.01) |
| *C07C 4/06* | (2006.01) |
| *C07C 5/11* | (2006.01) |
| *C07C 5/367* | (2006.01) |
| *C07C 6/12* | (2006.01) |
| *C07C 7/148* | (2006.01) |
| *B01J 29/08* | (2006.01) |
| *B01J 29/90* | (2006.01) |

(52) U.S. Cl.
CPC ............... *C07C 45/53* (2013.01); *C07C 407/00* (2013.01); *C07C 2/66* (2013.01); *C07C 4/06* (2013.01); *C07C 5/11* (2013.01); *C07C 5/367* (2013.01); *C07C 6/126* (2013.01); *C07C 7/1485* (2013.01); *C07C 37/08* (2013.01); *B01J 29/08* (2013.01); *B01J 29/90* (2013.01); *C07C 2101/14* (2013.01); *C07C 2101/16* (2013.01); *C07C 2521/04* (2013.01); *C07C 2521/06* (2013.01); *C07C 2521/12* (2013.01); *C07C 2521/16* (2013.01); *C07C 2523/06* (2013.01); *C07C 2523/14* (2013.01); *C07C 2523/30* (2013.01); *C07C 2523/44* (2013.01); *C07C 2523/46* (2013.01); *C07C 2523/75* (2013.01); *C07C 2523/755* (2013.01); *C07C 2527/053* (2013.01); *C07C 2527/173* (2013.01); *C07C 2529/08* (2013.01); *C07C 2529/18* (2013.01); *C07C 2529/70* (2013.01); *C07C 2529/84* (2013.01); *C07C 2529/85* (2013.01); *C07C 2529/89* (2013.01)
USPC ............ 568/342; 568/768; 568/798; 585/446

(58) Field of Classification Search
CPC .......... C07C 45/53; C07C 37/08; C07C 2/66; C07C 2529/08
USPC ................... 568/342, 570, 768, 798; 585/446
See application file for complete search history.

(56) References Cited

U.S. PATENT DOCUMENTS

| | | | |
|---|---|---|---|
| 3,959,381 | A | 5/1976 | Arkell et al. |
| 4,021,490 | A | 5/1977 | Hudson |
| 4,439,409 | A | 3/1984 | Puppe et al. |
| 4,490,565 | A | 12/1984 | Chang et al. |
| 4,490,566 | A | 12/1984 | Chang et al. |
| 4,826,667 | A | 5/1989 | Zones et al. |
| 4,870,217 | A | 9/1989 | Knifton |
| 4,954,325 | A | 9/1990 | Rubin et al. |
| 5,236,575 | A | 8/1993 | Bennett et al. |
| 5,250,277 | A | 10/1993 | Kresge et al. |
| 5,254,751 | A | 10/1993 | Zakoshansky |
| 5,362,697 | A | 11/1994 | Fung et al. |
| 6,014,018 | A | 1/2000 | Wu et al. |
| 6,037,513 | A | 3/2000 | Chang et al. |
| 6,049,018 | A | 4/2000 | Calabro et al. |
| 6,077,498 | A | 6/2000 | Diaz Cabañas et al. |

(Continued)

FOREIGN PATENT DOCUMENTS

| | | |
|---|---|---|
| EP | 0 293 032 | 11/1988 |
| JP | 2007-099745 | 4/2007 |

(Continued)

OTHER PUBLICATIONS

Baerlocher et al., "Framework type data FAU zeolites," Atlas of Zeolites Structure Types (5th Ed.), pp. 1-3 (2001).

(Continued)

*Primary Examiner* — Sikarl Witherspoon
(74) *Attorney, Agent, or Firm* — Siwen Chen; Jamie L. Sullivan

(57) ABSTRACT

In a process for producing phenol and cyclohexanone a feed comprising cyclohexylbenzene hydroperoxide and water in an amount from 1 to 15,000 ppm, based upon total weight of feed, is contacted with a cleavage catalyst comprising an aluminosilicate of the FAU type under cleavage conditions effective to convert at least a portion of the cyclohexylbenzene hydroperoxide into phenol and cyclohexanone.

25 Claims, No Drawings

(56) References Cited

U.S. PATENT DOCUMENTS

| | | |
|---|---|---|
| 6,720,462 B2 | 4/2004 | Kuhnle et al. |
| 6,756,030 B1 | 6/2004 | Rohde et al. |

FOREIGN PATENT DOCUMENTS

| | | |
|---|---|---|
| JP | 2007-099746 | 4/2007 |
| WO | 97/17290 | 5/1997 |
| WO | 2009/025939 | 2/2009 |
| WO | 2009/131769 | 10/2009 |
| WO | 2010/042261 | 4/2010 |
| WO | WO2011/001244 A1 * | 6/2011 |
| WO | 2012/145028 | 10/2012 |
| WO | 2012/145029 | 10/2012 |
| WO | 2012/145030 | 10/2012 |
| WO | 2012/145031 | 10/2012 |

OTHER PUBLICATIONS

Koltunov, et al., *"Efficient Cleavage of Cumene Hydroperoxide over HUSY Zeolites: The Role of Bronsted Acidity,"* Applied Catalysis A: General, 2008, vol. 336, pp. 29-34.

Periodic Table of the Elements, Chemical and Engineering News, vol. 63, No. 5, p. 27 (1985).

* cited by examiner

METHOD FOR PRODUCING PHENOL AND/OR CYCLOHEXANONE

PRIORITY CLAIM TO RELATED APPLICATIONS

This application is a National Stage Application of International Application No. PCT/US2011/065063 filed Dec. 15, 2011, which claims priority to U.S. Provisional Application Ser. No. 61/476,893 filed Apr. 19, 2011, the disclosures of which are fully incorporated herein by their reference.

CROSS REFERENCE TO RELATED PATENT APPLICATIONS

This application is related to U.S. Provisional Application Ser. No. 61/502,985 filed Jun. 30, 2011, U.S. Provisional Application Ser. No. 61/502,979 filed Jun. 30, 2011, U.S. Provisional Application No. 61/509,258 filed Jul. 19, 2011.

FIELD

This invention relates to a method for producing phenol and/or cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide generally in the presence of a sulfuric acid catalyst into equimolar amounts of phenol and acetone, a co-product.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide which is then decomposed to the desired phenol and cyclohexanone co-product.

In the cumene-based Hock process, dilute cumene hydroperoxide from the cumene oxidation step is first concentrated to greater than 80 wt % by removing unreacted cumene under vacuum, and the resultant concentrate is then sent to the cleavage reactor. In addition to the hazards associated with handling concentrated hydroperoxide, the cleavage poses safety concerns due to the rapid and highly exothermic nature of the reaction. Further, significant amounts of by-products may be generated from the concentrated oxidation products. In practice, therefore, the concentrated cumene hydroperoxide is often diluted with solvents, such as acetone, in order to better manage the heat of reaction and to control by-product formation. For example, U.S. Pat. No. 5,254,751 discloses a method of producing phenol and acetone by decomposing cumene hydroperoxide in a non-isothermal manner in the presence of excess acetone whereby the molar ratio of acetone to phenol in a decomposition reactor is from about 1.1:1 to 1.5:1.

In producing phenol from cyclohexylbenzene, the problems are different. Firstly, oxidation of cyclohexylbenzene to cyclohexylbenzene hydroperoxide is much more difficult than oxidation of cumene and requires elevated temperatures and the use of a catalyst, such as N-hydroxyphthalimide (NHPI). As a result, the cyclohexylbenzene oxidation effluent is also generally at elevated temperatures so that cooling this stream back to ambient temperature would incur additional operating cost. Also, in view of the high boiling point of cyclohexylbenzene, concentration of the cyclohexylbenzene hydroperoxide by evaporation of the unreacted cyclohexylbenzene is difficult and can lead to unwanted decomposition of the hydroperoxide. Thus, with cyclohexylbenzene hydroperoxide cleavage, the feed contains about 80 wt % hydrocarbon and the products contain only about 20 wt % polar components, which limits sulfuric acid solubility and the cleavage rate. In addition, the cleavage chemistry for cyclohexylbenzene hydroperoxide is much more complicated than that for cumene hydroperoxide, particularly since more routes for by-product formation exist with cyclohexylbenzene hydroperoxide cleavage. Moreover, cyclohexanone is much more prone to acid-catalyzed aldol condensation reactions than acetone so that significant yield loss is possible unless the cyclohexylbenzene hydroperoxide cleavage is closely controlled.

There are other disadvantages of using sulfuric acid for cyclohexylbenzene hydroperoxide cleavage: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal and the waste water needs to be treated. Therefore, there are strong incentives to replace sulfuric acid with a heterogeneous cleavage catalyst that eliminates these drawbacks.

The patent and academic literature is replete with suggestions for replacing sulfuric acid in the cleavage of cumene hydroperoxide. For example, U.S. Pat. No. 4,490,565 discloses that zeolite beta is an effective replacement for sulfuric acid in the cleavage of cumene hydroperoxide and indicates that the yields, conversions and selectivities are generally superior to those produced by the use of the large pore zeolites X and Y. In U.S. Pat. No. 4,490,566, similar improvements over the large pore zeolites X and Y are reported with intermediate pore size zeolites, such as ZSM-5. In contrast, in an article entitled "Efficient Cleavage of Cumene Hydroperoxide over HUSY zeolites: The role of Bronsted activity," *Applied Catalysis A: General*, 336 (2008), pages 29-34, Koltonov et al. report that cumene hydroperoxide readily undergoes decomposition over HUSY zeolites of high (15 to 40) Si/Al ratio with good selectivity to phenol and acetone and with efficiency even comparable to that of sulfuric acid. Despite or possibly because of these varying recommendations, most commercial processes for the cleavage of cumene hydroperoxide continue to use sulfuric acid as the catalyst.

Less interest has been focused on the cleavage of cyclohexylbenzene hydroperoxide, although International Patent Publication No. WO2011/001244 discloses that cyclohexylbenzene hydroperoxide can be converted to phenol and cyclohexanone in the presence of a variety of homogeneous or heterogeneous acid catalysts selected from protic acids and Lewis acids. Suitable homogeneous catalysts are said to include protic acids selected from sulfuric acid, phosphoric acid, chloride acid, p-toluenesulfonic acid, Amberlyst and Lewis acids are selected from ferric chloride, zinc chloride, boron trifluoride. Suitable heterogeneous acids are said to include zeolite beta, zeolite Y, zeolite X, ZSM-5, ZSM-12 and mordenite.

In addition, Japan Unexamined Patent Publication 2007-099746 discloses that cycloalkyl benzene hydroperoxides can be cleaved with high selectivity to phenol and cycloalkanone in the presence of montmorillonite, silica-alumina, cationic ion exchange resins, and sulfonic acid, perfluorosulfonic acid and heteropolyacids supported on a carrier. Similarly, Japan Unexamined Patent Publication 2007-099745 discloses that cycloalkyl benzene hydroperoxides can be cleaved with high selectivity to phenol and cycloalkanone in the presence of aluminosilicate zeolites having pore diameter of 0.6 nm or greater, such as zeolite Y and zeolite beta.

Moreover, in our co-pending U.S. Patent Application Ser. No. 61/476,893, which is not admitted to be prior art, we have disclosed a process for phenol and cyclohexanone by oxidizing cyclohexylbenzene in the presence of a cyclic imide catalyst to produce an oxidation effluent comprising cyclohexylbenzene hydroperoxide and then contacting the oxidation effluent with a cleavage catalyst comprising an aluminosilicate zeolite of the FAU type having a unit cell size less than 24.50 Å, such as less than or equal to 24.45 Å. This application also discloses subjecting the oxidation effluent to water washing and then passing it through an adsorbent, such as a 3A molecular sieve, to remove water and other adsorbable compounds, to provide an oxidation composition with reduced water and/or imide content that is subjected to the cleavage reaction.

According to the present invention, it has now been surprisingly found that the addition of a small amount of water to the cleavage feed (i.e., <0.5 wt % relative to total weight of the feed) enhances selectivity to phenol and cyclohexanone in FAU catalyzed cleavage of cyclohexylbenzene peroxide.

SUMMARY

In one aspect, the invention resides in a process for producing phenol and cyclohexanone, the process comprising:

(a) contacting a feed comprising cyclohexylbenzene hydroperoxide and 1 to 15,000 ppm, such as from 10 to 10,000 ppm, such as from 100 to 5,000 ppm of water, based upon total weight of the feed, with a cleavage catalyst comprising an aluminosilicate of the FAU type under cleavage conditions effective to convert at least a portion of the cyclohexylbenzene hydroperoxide into phenol and cyclohexanone.

Conveniently, the feed comprises from 0.5 to 49.5 wt % cyclohexylbenzene hydroperoxide and greater than 50 wt % cyclohexylbenzene, based upon total weight of the feed.

In one embodiment, the FAU type zeolite has a unit cell size less than or equal to 24.35 Å, such as less than or equal to 24.30 Å.

Conveniently, the cleavage conditions include a temperature of about 20° C. to about 200° C. and a pressure of about 100 kPa, gauge to about 2000 kPa, gauge.

Conveniently, the contacting step (a) is conducted in at least one fixed bed reactor, more typically in at least a first reactor and a second reactor connected in series or in parallel.

In a further aspect, the invention resides in a process for producing phenol and cyclohexanone, the process comprising:

(a) contacting benzene and hydrogen in the presence of a hydroalkylation catalyst under hydroalkylation conditions effective to form a first effluent stream comprising cyclohexylbenzene;

(b) contacting at least a portion of the cyclohexylbenzene from the first effluent stream with oxygen in the presence of cyclic imide catalyst to form a second effluent stream comprising cyclohexylbenzene hydroperoxide and unreacted cyclohexylbenzene; and (c) contacting a feed comprising at least a portion of said cyclohexylbenzene hydroperoxide from (b) and water in an amount up to 15,000 ppm, based upon total weight of feed, with a cleavage catalyst comprising an aluminosilicate of the FAU type under cleavage conditions effective to convert at least a portion of the cyclohexylbenzene hydroperoxide into phenol and cyclohexanone.

DETAILED DESCRIPTION

Described herein is a process for producing phenol by cleavage of cyclohexylbenzene hydroperoxide in the presence of a catalyst comprising an aluminosilicate zeolite of the FAU type, wherein the cleavage feed also contains water in an amount up to 15,000 ppm, such as from 100 to 5,000 ppm. As will be discussed in more detail below, the presence of this small amount of water in the cleavage feed is found to enhance the selectivity of the reaction to phenol and cyclohexanone.

In one preferred embodiment, the present cleavage process forms part of an integrated process for producing phenol and cyclohexanone from benzene, in which the benzene is converted to cyclohexylbenzene, the cyclohexylbenzene is then oxidized to cyclohexylbenzene hydroperoxide and the cyclohexylbenzene hydroperoxide is cleaved to produce phenol and cyclohexanone. The present process will therefore now be more particularly described with reference to this preferred embodiment.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

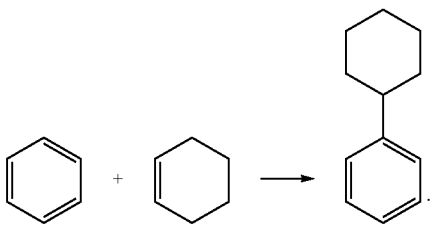 [SMILES: c1ccccc1 ; C1=CCCCC1 ; c1ccc(C2CCCCC2)cc1]

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

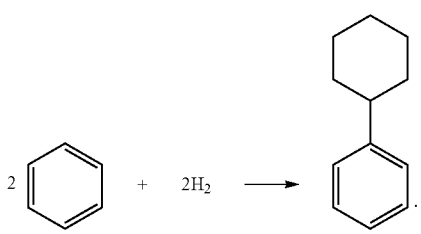 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100 to about 300° C., a pressure of about 800 kPa to about 3500 kPa, a weight hourly space velocity of about 1 to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as WO$_x$/ZrO$_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a C$_6$-rich stream comprising cyclohexane and unreacted benzene can be readily removed from the hydroalkylation reaction effluent by distillation, owing to the similarity in the boiling points of benzene and cyclohexane, the C$_6$-rich stream is difficult to further separate by simple distillation. However, some or all of the C$_6$-rich stream can be recycled to the hydroalkylation reactor to provide not only part of the benzene feed but also part of the diluents mentioned above.

In some cases, it may be desirable to supply some of the C$_6$-rich stream to a dehydrogenation reaction zone, where the C$_6$-rich stream is contacted with a dehydrogenation catalyst under dehydrogenation conditions sufficient to convert at least a portion of the cyclohexane in the C$_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 14.5 psig to 500 psig (100 kPa to 3550 kPa), a weight hourly space velocity of about 0.2 to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the C$_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene, and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

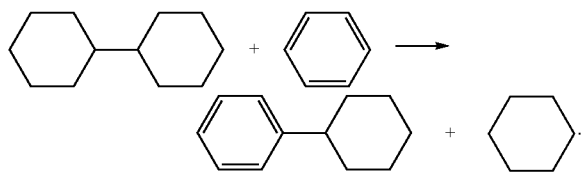

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is then subjected to a cleavage reaction, either directly or after undergoing prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate the imide oxidation catalyst (e.g., NHPI) and other adsorbable compounds, and provide an oxidation composition with a reduced imide content that may be subjected to the cleavage reaction. Similarly, all or a fraction of the oxidation effluent may undergo a chemically or physically based adsorption, such as passage over a bed of sodium carbonate to remove the imide oxidation catalyst and other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939, the entire contents of which are incorporated herein by reference.

In another embodiment, all or a fraction of the oxidation effluent may be contacted with an aluminosilicate zeolite of the FAU type to reduce the amount of unreacted imide catalyst in the effluent by adsorption onto the zeolite. The FAU type zeolite employed to remove the oxidation catalyst may be same as the FAU type zeolite employed in the cleavage reaction, namely having a unit cell size less than 24.50, or less than 24.45, or less than 24.40, or less than 24.35 Å, such as less than 24.30 Å, and the contacting to remove the oxidation catalyst can be conducted prior to or concurrently with the cleavage reaction. The adsorbed imide catalyst can be desorbed from the FAU type zeolite by washing with a polar solvent, such as acetone or cyclohexanone, and recovered by flashing off the solvent and/or by recrystallization. The recovered imide can then be recycled to the oxidation reaction.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

The acid catalyst used in the present cleavage reaction comprises a FAU-type zeolite having a unit cell size less than 24.50 Angstroms ("Å"), such as less than or equal to 24.45 Å, or less than or equal to 24.40 Å, or less than or equal to 24.35 Å, or less than or equal to 24.30 Å, or even less than or equal to 24.25 Å. Unit cell size is determined by X-ray diffraction as described in ASTM D-3942. As used herein, "FAU-type zeolite" or "zeolite of the FAU type" means a zeolite having a FAU-type structure as described in the *Atlas of Zeolite Framework Types*, Ch. Baerlocher et al. (6th Ed. 2007). The zeolite can be used in unbound form or can be combined with a binder, such as silica or alumina, such that the overall catalyst (zeolite plus binder) comprises from about 5 wt % to about 95 wt % of the zeolite.

In various embodiments, the cleavage catalyst loading (i.e., the amount of cleavage catalyst per unit amount of the cleavage feed mixture) is greater than 0.1 wt %, or greater than 0.5 wt %, or is greater than 1 wt %, or is greater than 2 wt %.

In various embodiments, the cleavage catalyst has a pore volume as measured by nitrogen ($N_2$) adsorption of greater than 0.3 cc/g, or greater than 0.4 cc/g, or greater than 0.5 cc/g. In various embodiments, the cleavage catalyst contains less than 6 wt %, or less than 3 wt %, or less than 1 wt %, or less than 0.5 wt % of Group 3 to Group 12 metals including the lanthanide series, based upon the weight of the catalyst.

The feed to the cleavage reaction generally contains from 0.5 to 49.5 wt %, such as from 10 to about 40 wt %, cyclohexylbenzene hydroperoxide and at least 50 wt %, such as from 50.5 to 99.5 wt %, unreacted cyclohexylbenzene. In addition, in the present process a small amount of water is present in the cleavage feed such that the feed contains from 1 to 15,000 ppm, such as from 10 to 10,000 ppm, such as from 100 to 5,000 ppm water based upon the total weight of the feed. In various embodiments, the lower limit of water in the cleavage reaction feed is 1 ppm, or 10 ppm, or 50 ppm, or 100 ppm, or 200 ppm, or 300 ppm, or 500 ppm, or 750 ppm, or 1,000 ppm, or 2,000 ppm, based upon the total weight of the feed. In various embodiments, the upper limit of water in the cleavage reaction feed is 20,000 ppm, or 17,500 ppm, or 15,000 ppm, or 10,000 ppm, or 7,500 ppm, or 5,000 ppm, or 4,000 ppm, based upon the total weight of the feed. It will be understood that the amount of water in the cleavage reaction feed may be any combination of the lower and upper limits described herein.

The addition of the water is found to increase the selectivity of the conversion of the cyclohexylbenzene hydroperoxide to phenol and cyclohexanone. Although the mechanism is not fully understood, it is believed that the water reduces the free radical induced conversion of the cyclohexylbenzene hydroperoxide to undesired products such as hexanophenone and phenylcyclohexanol. Additionally, since cyclohexanone aldol condensation is equilibrium-limited that generates water from the reaction, adding water can therefore inhibit aldol condensation thus mitigating cyclohexanone yield loss via aldol condensation.

Generally, the cleavage reaction is conducted under conditions including a temperature of about 20° C. to about 200° C., such as about 40° C. to about 120° C. and a pressure of about 100 kPa, gauge to about 2000 kPa, gauge, such as about 100 kPa, gauge to about 1000 kPa, gauge, such that the cleavage reaction mixture is completely or predominantly in the liquid phase during the cleavage reaction. The weight hourly space velocity may be about $1\ h^{-1}$ to about $1000\ h^{-1}$ on total feed, preferably from $1\ h^{-1}$ to about $500\ h^{-1}$, and more preferably from about $1\ h^{-1}$ to $300\ h^{-1}$.

The cleavage reaction can be conducted in a variety of reactor configurations and in either a single reactor or in a plurality of reactors. For example, the reaction may be conducted at least a first reactor and a second reactor connected in series, with the first reactor being operated at a temperature of about 20° C. to about 120° C. and a pressure of about 100 kPa, gauge to about 500 kPa, gauge and the second reactor being operated at a temperature of about 40° C. to about 180° C. and a pressure of about 100 kPa, gauge to about 1000 kPa, gauge. The first and second reactors may be the same or different and may also be connected in parallel.

In one embodiment, the cleavage reaction is conducted in a slurry reactor, such as a stirred tank, pump-around loop or other suitable configuration. In one embodiment, at least a portion of the cleavage reaction is conducted in a continuous stirred tank reactor (CSTR), with the catalyst being slurried in the cleavage reaction medium. Typically, the catalyst is added in an amount between about 50 wppm and about 20,000 wppm of the cleavage reaction medium. Advantages for this configuration include easy heat management and flexibility to add/withdraw catalyst to maintain conversion as the catalyst deactivates. If peroxide cleavage is performed with the oxidation product containing the imide catalyst, the latter will adsorb on the catalyst, inhibiting its performance. The imide catalyst adsorbed on the catalyst can be removed or recovered by recovering the imide-loaded catalyst from the cleavage reactor and washing this spent catalyst with a polar solvent such as acetone or cyclohexanone to recover its cleavage activity and imide adsorbing capacity (rejuvenation of the catalyst). The deactivated catalyst can be also regenerated by burning off coke in air. In case the catalyst is also used for recovery of the imide catalyst, this air-regeneration advantageously performed after recovering the adsorbed catalyst. In a slurry cleavage process, the catalyst can be regenerated on various schedules. Advantageously, the catalyst would be continuously withdrawn from the cleavage reactor, regenerated in an external recycle loop, and then returned into the cleavage reactor. Under such operation regime, a steady state of catalyst activity can be maintained through regeneration and by continuously replacing a fraction of the recycled catalyst with fresh catalyst.

The FAU catalyst can also be used in a fixed bed plug-flow reactor with or without first removing the imide catalyst from the cleavage feed stream. If the imide catalyst is not removed, the FAU bed adsorbs it, allowing its recovery and recycle to the oxidation process. In such a process design, two or more parallel cleavage reactor trains may be deployed to enable uninterrupted processing of the peroxide feed. Thus, as the FAU catalyst is saturated with the imide catalyst causing it to deactivate in one reactor train, the cleavage feed is switched to another reactor train that contains fresh or regenerated catalyst. The imide-saturated catalyst can be rejuvenated off-line by, for example, flushing with a polar solvent such as acetone or cyclohexanone. The imide catalyst recovered can be re-used for oxidation. The coke on catalyst can then also be removed by burning in air before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

The cleavage reaction using the FAU-type zeolite catalyst may have a cyclohexylbenzene hydroperoxide conversion of greater than 30%, or greater than 50%, or greater than 70%, or greater than 90%, or greater than 95%, or greater than 99%, or even 100%. The phenol selectivity may be greater than 60%, or greater than 70%, or greater than 90%, or greater than 95%. The cyclohexanone selectivity may be greater than 27%, or greater than 50%, or greater than 70%, or greater than 80%, or greater than 85%, or greater than 90%. As used herein, "cyclohexylbenzene hydroperoxide conversion" means the amount of cyclohexylbenzene hydroperoxide converted to any product. "Phenol selectivity" is relative to the theoretical phenol selectivity based upon the amount of cyclohexylbenzene hydroperoxide converted. "Cyclohexanone selectivity" is relative to the theoretical cyclohexanone selectivity based upon the amount of cyclohexylbenzene hydroperoxide converted.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following non-limiting Examples.

EXAMPLE 1

Oxidation of Cyclohexylbenzene

An amount of 631 g of cyclohexylbenzene (CHB, TCI America, Inc.) was added to a 1-liter four-necked glass flask, to which 0.6702 g of NHPI (TCI America, Inc.) was added. The flask was then fitted with a reflux condenser, a mechanical stirrer, a gas sparger, and a thermometer. An air flow of 250 cc/min was bubbled through the liquid via the gas sparger; and the contents were heated at 110° C. with stirring (560 rpm) for 6 hours. The flask was allowed to cool down to room temperature and the oxidation product recovered. GC analysis indicated the product to contain 17.9 wt % cyclohexylbenzene hydroperoxide (CHBHP).

EXAMPLE 2

Removal of NHPI from CHB Oxidation Products

An amount of 300 g of the oxidation products from Example 1 was placed in a 500-mL glass flask and mixed with 30 g of anhydrous sodium carbonate (granular form, Aldrich). The mixture was stirred overnight and the solid became brick-red in color. The solid was then removed by filtration and the liquid further filtered through a bed of anhydrous magnesium sulfate. A clear, light-yellow liquid was obtained. GC analysis revealed the product to contain 17.5% CHBHP.

EXAMPLE 3

Cleavage of CHBHP (~3 Wt % CHBHP) Using FAU in Batch Operation

An amount of 30 g mixture of CHBHP/CHB/phenol/cyclohexanone (about 3/81/8/8 wt. ratio) and dodecane (for mass balance purposes) was charged to a 50-mL jacketed glass reactor with a circulating temperature bath. The bath was set to the desired temperature of 60° C. and the reactor contents were allowed to equilibrate. Once the temperature stabilized a GC sample was taken for the hot feed. The desired amount of FAU type zeolite (see Table 1), as supplied by Zeolyst International as CBV760, was then added to the mixture. After a brief reaction exotherm, as indicated by the temperature rise inside the reactor, a 1-mL aliquot was taken at certain time interval and the solid filtered. The samples generated were analyzed by GC and the results are summarized in Table 1.

EXAMPLE 4

Cleavage of CHBHP (~3 Wt % CHBHP) Using FAU with Addition of Water to the Feed in Batch Operation An amount of 30 g mixture of CHBHP/CHB/phenol/cyclohexanone (about 3/81/8/8 wt. ratio) and dodecane (for mass balance purposes) was charged to a 50-mL jacketed glass reactor with a circulating temperature bath. A desired amount of water (see Table 1) was then added to the feed. The bath was set to the desired temperature of 60° C. and the reactor contents were allowed to equilibrate. Once the temperature stabilized, a GC sample was taken for the hot feed. The desired amount of CBV760 (see Table 1) was then added to the mixture. After a brief reaction exotherm, as indicated by the temperature rise inside the reactor, a 1-mL aliquot was taken at certain time interval and the solid filtered. The samples generated were analyzed by GC and the results are summarized in Table 1.

TABLE 1

| Catalyst loading (wt %) | Water added (ppm) | CHBHP conversion (%) | Phenol selectivity (%) | Cyclohexanone selectivity (%) |
|---|---|---|---|---|
| 0.5 | 0 | 98 | 99 | 84 |
| 0.5 | 2000 | 98 | 99 | 84 |
| 0.5 | 4000 | 98 | 99 | 88 |
| 2 | 0 | 98 | 96 | 93 |
| 2 | 2000 | 99 | 99 | 94 |
| 2 | 4000 | 99 | 99 | 94 |

It can be seen from Table 1 that presence of water enhances selectivity for FAU-catalyzed CHBHP cleavage.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol and cyclohexanone, the process comprising:
   (a) contacting a feed comprising cyclohexylbenzene hydroperoxide and 1 ppm to 15,000 ppm of water, based upon total weight of the feed, with a cleavage catalyst comprising an aluminosilicate of the FAU type under cleavage conditions effective to convert at least a portion of the cyclohexylbenzene hydroperoxide into phenol and cyclohexanone.

2. The process of claim 1, wherein the water is present in said feed in an amount ranging from 10 to 10,000 ppm based upon total weight of feed.

3. The process of claim 1, wherein water is present in said feed in an amount ranging from 100 to 5,000 ppm based upon total weight of feed.

4. The process of claim 1, wherein the feed comprises from 0.5 wt % to 49.5 wt % cyclohexylbenzene hydroperoxide, based upon total weight of the feed.

5. The process of claim 1, wherein the feed comprises at least 50 wt % cyclohexylbenzene, based upon total weight of the feed.

6. The process of claim 1, wherein the FAU type zeolite has a unit cell size less than or equal to 24.35 Å.

7. The process of claim 1, wherein the FAU type zeolite has a unit cell size less than or equal to 24.30 Å.

8. The process of claim 1, wherein the cleavage conditions include a temperature of about 20° C. to about 200° C. and a pressure of about 100 kPa, gauge to about 2000 kPa, gauge.

9. The process of claim 1, wherein the contacting step (a) is conducted in at least one fixed bed reactor.

10. The process of claim 1, wherein the contacting step (a) is conducted in at least a first reactor and a second reactor connected in series.

11. The process of claim 1, wherein the contacting step (a) is conducted in at least a first reactor and a second reactor connected in parallel.

12. The process of claim 1, comprising a cleavage catalyst loading of greater than 0.1 wt %, the percentage being expressed as an amount of cleavage catalyst per amount of feed.

13. The process of claim 1, wherein the cleavage catalyst is continuously or periodically added to the contacting step (a) to maintain conversion at a given level.

14. A process for producing phenol and cyclohexanone, the process comprising:
   (a) contacting benzene and hydrogen in the presence of a hydroalkylation catalyst under hydroalkylation conditions effective to form a first effluent stream comprising cyclohexylbenzene;
   (b) contacting at least a portion of the cyclohexylbenzene from the first effluent stream with oxygen in the presence of cyclic imide catalyst to form a second effluent stream comprising cyclohexylbenzene hydroperoxide and unreacted cyclohexylbenzene; and
   (c) contacting a feed comprising at least a portion of said cyclohexylbenzene hydroperoxide from (b) and water in an amount up to 15,000 ppm, based upon total weight of feed, with a cleavage catalyst comprising an aluminosilicate of the FAU type under cleavage conditions effective to convert at least a portion of the cyclohexylbenzene hydroperoxide into phenol and cyclohexanone.

15. The process of claim 14, wherein water is present in said feed in an amount ranging from 100 ppm to 5,000 ppm based upon total weight of feed.

16. The process of claim 14, wherein the feed comprises from 0.5 wt % to 49.5 wt % cyclohexylbenzene hydroperoxide, based upon total weight of the feed.

17. The process of claim 14, wherein the feed comprises at least 50 wt % unreacted cyclohexylbenzene, based upon total weight of the feed.

18. The process of claim 14, wherein the FAU type zeolite has a unit cell size less than or equal to 24.35 Å.

19. The process of claim 14, wherein the FAU type zeolite has a unit cell size less than or equal to 24.30 Å.

20. The process of claim 14, wherein the cleavage conditions include a temperature of about 20° C. to about 200° C. and a pressure of about 100 kPa, gauge to about 2000 kPa, gauge.

21. The process of claim 14, wherein the contacting step (c) is conducted in at least one fixed bed reactor.

22. The process of claim 14, wherein the contacting step (c) is conducted in at least a first reactor and a second reactor connected in series.

23. The process of claim 14, wherein the contacting step (c) is conducted in at least a first reactor and a second reactor connected in parallel.

24. The process of claim 14, comprising a cleavage catalyst loading of greater than 0.1 wt %, the percentage being expressed as an amount of cleavage catalyst per amount of feed.

25. The process of claim 14, wherein the cleavage catalyst is continuously or periodically added to the contacting step (c) to maintain conversion at a given level.

* * * * *